(12) United States Patent
Yellepeddi

(10) Patent No.: US 10,617,682 B2
(45) Date of Patent: Apr. 14, 2020

(54) PRESERVATIVE-FREE PROCHLORPERAZINE NASAL SPRAY FOR MIGRAINE THERAPY

(71) Applicant: ROSEMAN UNIVERSITY OF HEALTH SCIENCES, South Jordan, UT (US)

(72) Inventor: Venkata Kashyap Yellepeddi, South Jordan, UT (US)

(73) Assignee: Roseman University of Health Sciences, Las Vegas, NV (US)

( * ) Notice: Subject to any disclaimer, the term of this patent is extended or adjusted under 35 U.S.C. 154(b) by 0 days.

(21) Appl. No.: 15/994,582

(22) Filed: May 31, 2018

(65) Prior Publication Data

US 2018/0344720 A1     Dec. 6, 2018

Related U.S. Application Data

(60) Provisional application No. 62/513,669, filed on Jun. 1, 2017.

(51) Int. Cl.

| | |
|---|---|
| *A61K 31/4515* | (2006.01) |
| *A61K 47/02* | (2006.01) |
| *A61K 9/00* | (2006.01) |
| *A61K 9/08* | (2006.01) |
| *A61K 47/12* | (2006.01) |
| *A61P 25/06* | (2006.01) |

(52) U.S. Cl.
CPC ........ *A61K 31/4515* (2013.01); *A61K 9/0043* (2013.01); *A61K 9/08* (2013.01); *A61K 47/02* (2013.01); *A61K 47/12* (2013.01); *A61P 25/06* (2018.01)

(58) Field of Classification Search
CPC .... A61K 31/4515; A61K 47/02; A61K 47/12; A61K 9/0043; A61K 9/08; A61K 31/5415; A61P 25/06
See application file for complete search history.

(56) References Cited

U.S. PATENT DOCUMENTS

2010/0215730 A1\*   8/2010   Guy .................... A61K 9/0043
                                                                                    424/450

\* cited by examiner

*Primary Examiner* — Sarah Pihonak
(74) *Attorney, Agent, or Firm* — Hogan Lovells US LLP

(57) ABSTRACT

Embodiments relate to compositions comprising a prochlorperazine compound and a nasal carrier, including methods for formulating such compositions for pharmaceutical applications, for example, for treating or reducing the incidence of migraine headaches. Additional embodiments relate to articles comprising a prochlorperazine compound and a nasal carrier, including use of such articles as nasal drops or nasal sprays. Further embodiments relate to methods for using such articles, for example, for treating or reducing the incidence of migraines.

17 Claims, 3 Drawing Sheets

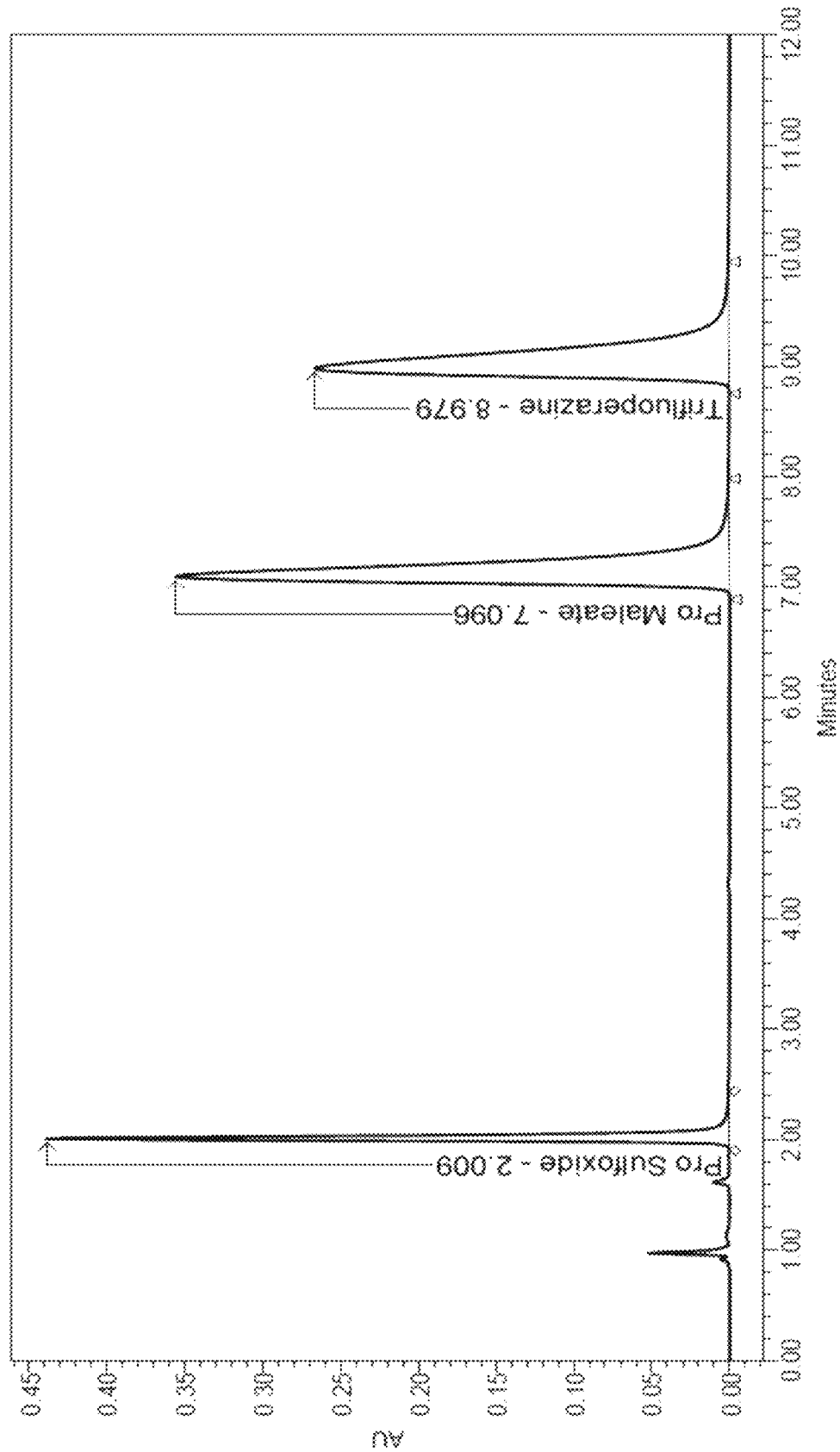
FIG. 1: HPLC chromatogram of prochlorperazine sulfoxide. Prochlorperazine is USP standard for prochlorperazine edisylate and Trifluoperazine is internal standard.

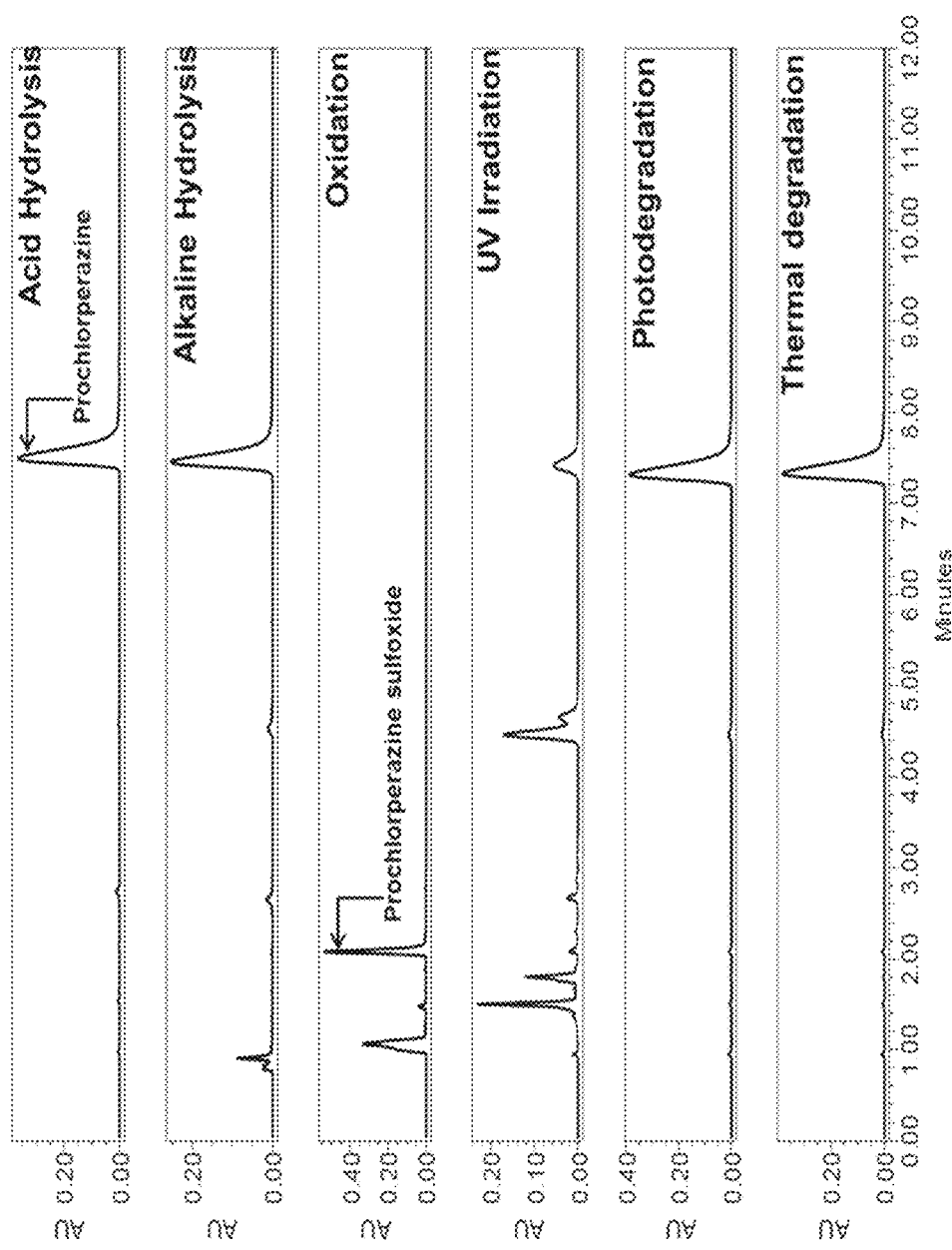
FIG. 2: Chromatograms representing forced degradation of 0.1 mg/mL prochlorperazine edisylate by (from top to bottom) acid hydrolysis (0.1 N Hydrochloric acid), alkaline hydrolysis (0.1 M sodium hydroxide), oxidation (0.1 M hydrogen peroxide), ultraviolet irradiation, photodegradation, and thermal degradation (60° C).

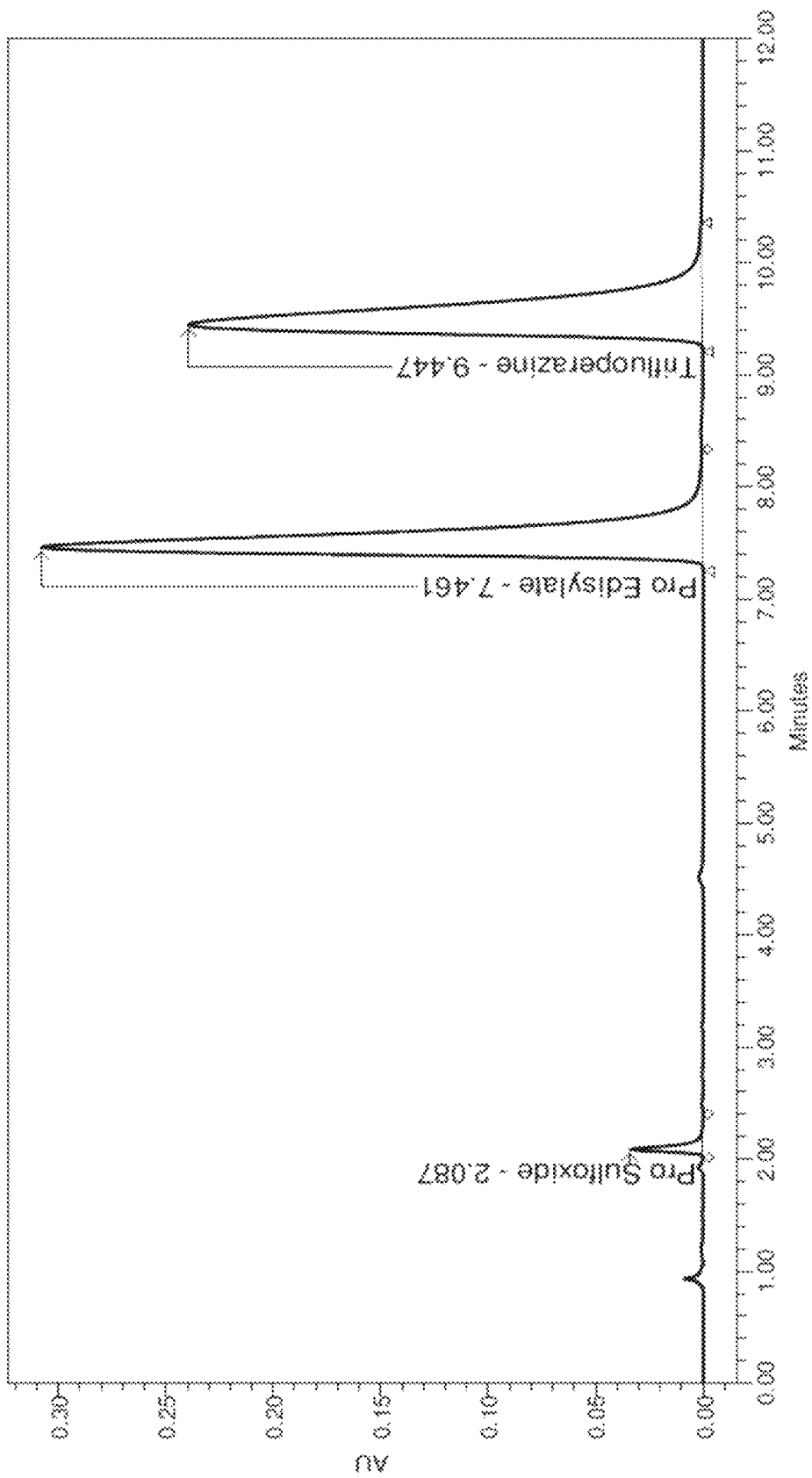
FIG. 3: HPLC chromatogram of 120-day stability sample from preservative-free prochlorperazine nasal spray. Prochlorperazine sulfoxide id the degradation product and Trifluoperazine is internal standard.

PRESERVATIVE-FREE PROCHLORPERAZINE NASAL SPRAY FOR MIGRAINE THERAPY

RELATED APPLICATIONS

This application claims the benefit of U.S. Provisional Application No. 62/513,669, filed on Jun. 1, 2017, the entire teachings of the above application is incorporated herein by reference.

TECHNICAL FIELD

Embodiments of the instant invention are directed to preservative-free compositions and formulations containing prochlorperazine. In other embodiments, the instant invention is directed to methods for treating migraines in subjects by administering the compositions or formulations containing such prochlorperazine compounds.

BACKGROUND OF THE INVENTION

A migraine is a type of a headache with characteristic throbbing pain which may occur with symptoms such as nausea, vomiting, or sensitivity to light. In the United States, more than 37 million people suffer from migraines and almost 5 million experience at least one migraine attack per month. The World Health Organization ranks migraines as the 19th most common reason for disability. The loss of productivity due to migraines is estimated to be between $5.6 billion to $17.2 billion per year because of missed work. See, Miles et al. "Migraine statistics," November 2010. Drugs commonly prescribed for the treatment of migraines include narcotic analgesics (oxycodone), non-steroidal anti-inflammatory drugs (ibuprofen), barbiturates (butalbital), ergot derivatives (dihydroergotamine), selective 5-HT receptor agonists (sumatriptan) and antiemetics (prochlorperazine). See, Zhang et al., *Ann Transl Med.* 2016; 4(6): 105; Goadsby et al., *Nat Rev Neurol.* 2015; 11(11): 621-2. A major drawback with the frequent use of narcotics is the risk of physical dependence and the "interdose withdrawal" phenomenon, which can lead to more migraines (Peroutka et al., *Headache.* 1990; 30(1 Suppl): 5-11; discussion 24-8; Jones et al., *Ann Emerg Med.* 1994; 24(2): 237-41). The chronic use and abuse of ergot alkaloids can result in ergot-induced headaches, which can worsen nausea and vomiting associated with a migraine as well as increase the risk of ergotism (Jones et al., supra; Kudrow et al., *Adv Neurol.* 1982; 33: 335-41). Even though therapy involving sumatriptan meets the majority of patient needs, patients often are not satisfied due to the development of rebound headaches, persistent nausea, vomiting, and gastric stasis (Sharma et al., *Headache.* 2002; 42(9): 896-902; Zed et al., *Ann Pharmacother.* 1999; 33(1): 61-72). This dissatisfaction indicates a clear need for alternative treatments for acute therapy of migraine headaches.

Prochlorperazine belongs to the piperazine subclass of phenothiazines and is widely used as an anti-emetic and anti-psychotic agent (Khatri et al., *Headache.* 2009; 49(3): 477-80). The most common degradation pathways of prochlorperazine involve oxidation and photodegradation resulting in sulfoxides as the major degradation products. Prochlorperazine is also used for migraines, and comparative clinical studies have shown that prochlorperazine provides better pain relief than sumatriptan, metoclopramide, and ketorolac (Jones et al., *Am J Emerg Med.* 1996; 14(3): 262-4; Seim et al., *Acad Emerg Med.* 1998; 5(6): 573-6; Donohue et al., *Ann Emerg Med.* 1995; 25: 154-55). Prochlorperazine was also shown to be highly effective in the treatment of acute confusional migraine which is a rare migraine variant primarily seen in childhood that lacks standardized diagnostic criteria (Khatri et al., *Headache.* 2009; 49(3): 477-80). For the treatment of acute migraine, prochlorperazine is usually administered at doses 10 mg by intravenous or intramuscular route and, 25 mg by oral or rectal route (Gelfand et al., *Neurohospitalist.* 2012; 2(2): 51-59). The exact mechanism of prochlorperazine for migraines is unknown. However, it is believed that prochlorperazine may exert effects for migraines by a combination of actions including anti-serotonin effects, anti-dopamine effects in the chemoreceptor trigger zone, and vascular effects through their α-blocking action (Lance et al., *Pathol Biol (Paris).* 1992; 40(4): 355-60). In all clinical trials discussed above, prochlorperazine was administered parenterally (intravenous, intramuscular, etc.) which is an expensive and cumbersome route of administration requiring medical intervention in a clinical setting.

The drawbacks of low and variable absorption and high first-pass metabolism limit administration of prochlorperazine by the oral route (Finn et al., *J Clin Pharmacol.* 2005; 45(12): 1383-90). Although nasally administered antiemetic formulations containing metoclopramide, ondansetron, granisetron, domperidone, dimenhydrinate and/or promethazine have been described in literature (Ozsoy et al., *Expert Opin Drug Deliv.* 2011; 8(11): 1439-53), they are formulated with a host of polymers such as poloxamer 405, pluronic 127, gellan gum, sodium carboxymethyl cellulose, carbopol 981, chitosan, etc., binders and solvents such as hydroxypropyl cellulose, polyvinyl alcohol, hydroxypropyl methylcellulose, sodium alginate, bile salts, protamine sulfate and poly-L-arginine, and other permeation enhancers (see, Ozsoy et al.). This review article is silent as to the unique advantages offered by aqueous formulations containing chlorperazine and the carriers described herein, including, ease of extemporaneous formulation and/or administration.

In certain instances, prochlorperazine may also be administered intravenously, parenterally or bucally; however, each route of administration is associated with numerous drawbacks. For instance, prochlorperazine, when administered intravenously, displays dose-dependent extrapyramidal side effects such as akathisia and tardive dyskinesia (Drotts et al., *Ann Emerg Med.* 1999; 34(4 Pt 1): 469-75). Parenteral administration is frequently associated with needle-stick injuries (Corrigan et al., *Am J Health Syst Pharm.* 2015; 72(18): 1544-54). In contrast to the existing modes of delivery, the instant invention contemplates that intranasal administration may offer several advantages, including, mitigating the risk of injuries; allowing self-treatment by patients for continuous therapy supplementing intravenous treatment in the emergency room; and reduction in extrapyramidal side effects due to delivery of high concentration of the drug at the target site (e.g., brain). Due to these potential benefits, intranasal administration of prochlorperazine may be an attractive alternative therapeutic option for treatment of an acute migraine in human patients.

Because nasally-administered prochlorperazine comes into direct contact with the soft tissues of the nasal mucosa, aqueous-based nasal sprays are preferably formulated as sterile formulations. Other anti-emetic nasal sprays are frequently formulated with preservatives such as benzalkonium chloride, methyl paraben, propyl paraben and phenylcarbinol, etc., which prevent antimicrobial contamination in (Batts et al., *J Pharm Pharmacol.* 1989; 41(3): 156-9). However, clinical evidence shows that preservatives such as benzalkonium chloride and phenylcarbinol may cause local mucosal hypersensitivity, including toxic effects such as sinonasal mucosal injury, nasal squamous metaplasia, and genotoxicity (Ho et al., *Am J Rhinol.* 2008; 22(2): 125-9; Deutschle et al., *Toxicol In vitro.* 2006; 20(8): 1472-7; Larsen et al., *Food Chem Toxicol.* 2003; 41(3): 439-46; Grummt et al., *Environ Mol Mutagen.* 2006; 47(2): 95-106). Thus, a need exists for formulating nasal sprays without the use of chemical preservatives, wherein the formulations have reduced toxicity compared to preservative-containing formulations, but are bioequivalent with respect to the desired pharmacological effects (e.g., potency, efficacy, etc.) even after storage for prolonged periods of time.

SUMMARY OF THE INVENTION

Embodiments of the invention described herein provide for compositions and methods of treating migraine. The present invention improves upon exiting methods by providing compositions that have been formulated for nasal delivery of the active ingredients.

It is therefore an object and advantage of the present invention to provide targeted delivery of therapeutic compositions for the treatment of migraine.

It is also an object and advantage of the present invention to provide compositions that are preservative-free, which help reduce or eliminate the side effects observed with the use of preservatives in pharmaceutical products, e.g., headaches, palpitations, allergies, and even cancer.

In accordance with the foregoing, embodiments of the present invention provide compositions that are stable and free of degradation products, with potencies that are comparable to, or even exceed, standard pharmaceutical grade preparations.

In particular, embodiments described herein provide for aqueous pharmaceutical preparations that can be prepared quickly and extemporaneously. Surprisingly, it was found that the compositions and formulations of the invention are physically, chemically, and microbiologically stable for extended periods with little or no loss of potency even after weeks of storage at room temperature.

Embodiments of the invention further relate to advantageously treating CNS disorders such as migraines. For instance, the instant compositions and methods may help eliminate or reduce variability in absorption and high first-pass metabolism associated with oral delivery of drugs such as prochlorperazine. Additionally, the extrapyramidal side effects such as akathisia and tardive dyskinesia, which are associated with intravenous delivery of prochlorperazine, may also be greatly reduced. Moreover, the instant compositions and formulations may further confer rapid and extensive drug absorption and increased patient adherence, while simultaneously minimizing the risk of needle-stick injuries associated with parenteral administration. Finally, the devices and methods described herein may permit self-treatment by patients and can be considered as an alternative therapeutic option for continuous therapy for patients discharged from the emergency department after intravenous treatment for a migraine.

In one embodiment, the instant invention provides for preservative-free pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier.

In another embodiment, the instant invention provides for preservative-free, aqueous pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier.

In another embodiment, the instant invention provides for a preservative-free, aqueous pharmaceutical composition which is a colorless and clear solution containing no visible particulate matter, and which comprises, as active ingredient, prochlorperazine or a derivative thereof or a salt thereof, or a hydrate thereof or an alcoholate thereof, or tautomer thereof, or a stereoisomer thereof and a nasal carrier.

In another embodiment, the instant invention provides for preservative-free pharmaceutical compositions comprising, as active ingredient, prochlorperazine or an edisylate salt thereof, or a hydrate thereof or an alcoholate thereof, or tautomer thereof, or a stereoisomer thereof and a nasal carrier.

In another embodiment, the instant invention provides for preservative-free pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier comprising an aqueous solution of citric acid and sodium chloride.

In another embodiment, the instant invention provides for preservative-free pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier comprising about 0.005% to about 0.5% citric acid and sodium chloride. In a specific embodiment, the nasal carrier comprises about 0.01% citric acid.

In another embodiment, the instant invention provides for preservative-free pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier comprising citric acid and about 0.5% to about 2.0% sodium chloride. In a specific embodiment, the nasal carrier comprises about 0.9% sodium chloride.

In another embodiment, the instant invention provides for preservative-free pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier comprising an acidic aqueous solution of citric acid and sodium chloride. In one embodiment, the acidic aqueous solution of citric acid and sodium chloride comprises a pH from about 2.0 to about 4.0. In a particular embodiment, the acidic aqueous solution of citric acid and sodium chloride comprises a pH of about 2.5.

In a related embodiment, the instant invention provides for preservative-free pharmaceutical compositions consisting essentially of prochlorperazine or a derivative thereof or a salt thereof, or a hydrate thereof or an alcoholate thereof, or tautomer thereof, or a stereoisomer thereof and a nasal carrier. In another related embodiment, the instant invention provides for preservative-free pharmaceutical compositions consisting of prochlorperazine or a derivative thereof or a salt thereof, or a hydrate thereof or an alcoholate thereof, or tautomer thereof, or a stereoisomer thereof and a nasal carrier.

In another embodiment, the instant invention provides for preservative-free pharmaceutical compositions which are formulated in the form of a nasal spray or nasal drops, comprising, as active ingredient, prochlorperazine or a derivative thereof or a salt thereof, or a hydrate thereof or an alcoholate thereof, or tautomer thereof, or a stereoisomer thereof and a nasal carrier.

In yet another embodiment, the instant invention provides for preservative-free pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier, wherein the composition is free of preservatives selected from the group consisting of benzyl alcohol, benzalkonium chloride, benzethonium chloride, chlorobutanol, methylparaben, propyl paraben, ethylenediaminetetraacetic acid, chlorocresol, chlorhexidine, phenylmercuric nitrate, phenylmercuric borate, phenylmercuric acetate, and thiomersal, or a combination thereof. In one specific embodiment, the pharmaceutical composition is free of preservative is selected from the group consisting of benzalkonium chloride and phenylcarbinol, or a combination thereof.

In another embodiment, the instant invention provides for a nasal spray bottle comprising a preservative-free pharmaceutical composition comprising, as active ingredient, prochlorperazine or a derivative thereof or a salt thereof, or a hydrate thereof or an alcoholate thereof, or tautomer thereof, or a stereoisomer thereof and a nasal carrier.

In another embodiment, the instant invention provides for a kit comprising, in one or more packages, comprising, a pharmaceutically effective amount of an active ingredient comprising prochlorperazine or a derivative thereof or a salt thereof, or a hydrate thereof or an alcoholate thereof, or tautomer thereof, or a stereoisomer thereof and a nasal carrier, optionally together with instructions for formulating a nasal spray comprising the active ingredient.

In another embodiment, the instant invention provides for preservative-free pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier, wherein the potency of the pharmaceutical composition is greater than about 95% compared to a standard composition comprising prochlorperazine maleate. In a specific embodiment, the potency of the pharmaceutical composition is greater than about 99% compared to a standard composition comprising prochlorperazine maleate.

In another embodiment, the instant invention provides for preservative-free, aqueous pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier, wherein the aqueous composition has a tailing factor of less than 2. In a specific embodiment, the aqueous composition has a tailing factor of about 1.87.

In another embodiment, the instant invention provides for preservative-free, pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier, wherein the pharmaceutical composition is free of degradation products. In a specific embodiment, the pharmaceutical composition is free of prochlorperazine sulfoxide.

In another embodiment, the instant invention provides for preservative-free, aqueous pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier, wherein the aqueous composition is stable for up to 20 days. In one specific embodiment, the aqueous composition is stable for up to 30 days. In another specific embodiment, the aqueous composition is stable for up to 60 days.

In another embodiment, the instant invention provides for preservative-free, aqueous pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier, wherein the aqueous composition is stable against oxidation and photodegradation.

In another embodiment, the instant invention provides for preservative-free, aqueous pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier, wherein the aqueous composition is microbiologically stable. In one specific embodiment, the aqueous composition is microbiologically stable against bacterial, yeast or fungal growth. In another specific embodiment, the aqueous composition is microbiologically stable for up to 30 days. In yet another specific embodiment, the aqueous composition is microbiologically stable for up to 60 days.

In another embodiment, the instant invention provides for preservative-free pharmaceutical compositions comprising, as active ingredient, prochlorperazine or a derivative thereof or a salt thereof, or a hydrate thereof or an alcoholate thereof, or tautomer thereof, or a stereoisomer thereof and a nasal carrier, wherein the dose of the active ingredient is between about 1 mg to about 10 mg. In another embodiment, the dose of the active ingredient is between about 2 mg/ml to about 8 mg/ml. In one particular embodiment, the dose of the active ingredient is about 5 mg/ml.

In a related embodiment, the instant invention provides for methods of making one or more of the aforementioned pharmaceutical compositions, comprising mixing prochlorperazine or a derivative thereof or a salt thereof, or a hydrate thereof or an alcoholate thereof, or tautomer thereof, or a stereoisomer thereof with at least one nasal carrier. In one specific embodiment, the method may involve mixing a salt of prochlorperazine which is prochlorperazine edisylate with at least one nasal carrier. Particularly, in one embodiment, the method involves making a an aqueous pharmaceutical composition and method involves mixing one or more of the prochlorperazine compounds with a nasal carrier comprising an aqueous solution of citric acid and sodium chloride.

In another related embodiment, the instant invention provides for methods of making one or more of the aforementioned pharmaceutical compositions, comprising mixing prochlorperazine or a derivative thereof or a salt thereof, or a hydrate thereof or an alcoholate thereof, or tautomer thereof, or a stereoisomer thereof with at least one nasal carrier; and further buffering the aqueous composition with an acid to a pH from between 2.0 and 4.0. In one specific embodiment, the method involves buffering the aqueous composition with an acid to a pH of about 2.5.

In another related embodiment, the instant invention provides for methods of making one or more of the aforementioned pharmaceutical compositions, comprising mixing prochlorperazine or a derivative thereof or a salt thereof, or a hydrate thereof or an alcoholate thereof, or tautomer thereof, or a stereoisomer thereof with at least one aqueous nasal carrier; optionally buffering the aqueous composition with an acid to a pH from between 2.0 and 4.0; and sterile filtering the aqueous composition. Under this embodiment, the method may further comprise formulating the aqueous pharmaceutical composition for nasal spray or nasal drop application.

To understand the present disclosure, it will now be described by way of example, with reference to the accompanying drawings in which embodiments of the disclosures are illustrated and, together with the descriptions below, serve to explain the principles of the disclosure.

FIG. 1 shows HPLC chromatogram of prochlorperazine sulfoxide. Prochlorperazine maleate is USP standard for prochlorperazine edisylate and Trifluoperazine is internal standard.

FIG. 2 shows chromatograms representing forced degradation of 0.1 mg/mL prochlorperazine edisylate by (from top to bottom) acid hydrolysis (0.1 N Hydrochloric acid), alkaline hydrolysis (0.1 M sodium hydroxide), oxidation (0.1 M hydrogen peroxide), ultraviolet irradiation, photodegradation, and thermal degradation (60° C.).

FIG. 3 shows HPLC chromatogram of 120-day stability sample from preservative-free prochlorperazine nasal spray. Prochlorperazine sulfoxide is the degradation product and Trifluoperazine is the internal standard.

DETAILED DESCRIPTION

The various embodiments of the invention are further described in the numbered paragraphs below.

Compositions:

In one embodiment, the instant invention relates to a preservative-free composition comprising, as active ingredient, prochlorperazine or a derivative thereof or a salt thereof, or a hydrate thereof or an alcoholate thereof, or tautomer thereof, or a stereoisomer thereof and a nasal carrier. Prochlorperazine (COMPAZINE, STEMZINE, BUCCASTEM, PHENOTIL) is a compound that belongs to the phenothiazine class of antipsychotic agents. In some embodiments, the compound comprises the structure shown in Formula I. In another embodiment, the prochlorperazine compound is also known as 2-chloro-10-[3-(4-methylpiperazin-1-yl)propyl]phenothiazine).

Formula I

The terms "compound" and "compounds" as used herein refers to a compound encompassed by the generic formulae disclosed herein, any subgenus of those generic formulae, and any specific compounds within the generic and subgeneric formulae.

In another embodiment, the compositions of the invention comprise derivatives of the aforementioned prochlorperazine compounds. The term "derivative" as used herein includes salts, amides, esters, enol ethers, enol esters, acetals, ketals, orthoesters, hemiacetals, hemiketals, acids, bases, solvates, hydrates or prodrugs of the aforementioned compounds. Such derivatives may be readily prepared by those of skill in this art using known methods for such derivatization. In certain embodiments, the derivatives may be administered to animals or humans without substantial toxic effects and either are pharmaceutically active or are prodrugs.

In another embodiment, the compositions of the invention comprise salts of the aforementioned prochlorperazine compounds. The term "salt" includes salts derived from a variety of organic and inorganic counter ions well known in the art and include, by way of example, hydrochloric acid salt, a hydrobromic acid salt, a sulfuric acid salt, a phosphoric acid salt, a metaphosphoric acid salt, an acetic acid salt, a propionic acid salt, a hexanoic acid salt, a cyclopentanepropionic acid salt, a glycolic acid salt, a pyruvic acid salt, a lactic acid salt, a malonic acid salt, a succinic acid salt, a malic acid salt, a L-malic acid salt, a maleic acid salt, an oxalic acid salt, a fumaric acid salt, a trifluoroacetic acid salt, a tartaric acid salt, a L-tartaric acid salt, a citric acid salt, a benzoic acid salt, a 3-(4-hydroxybenzoyl)benzoic acid salt, a cinnamic acid salt, a mandelic acid salt, a methanesulfonic acid salt, an ethanesulfonic acid salt, a 1,2-ethanedisulfonic acid salt, a 2-hydroxyethanesulfonic acid salt, a benzenesulfonic acid salt, a toluenesulfonic acid salt, a 2-naphthalenesulfonic acid salt, a 4-methylbicyclo-[2.2.2]oct-2-ene-1-carboxylic acid salt, a glucoheptonic acid salt, a 4,4'-methylenebis-(3-hydroxy-2-ene-1-carboxylic acid) salt, a 3-phenylpropionic acid salt, a trimethylacetic acid salt, a tertiary butylacetic acid salt, a lauryl sulfuric acid salt, a gluconic acid salt, a glutamic acid salt, a hydroxynaphthoic acid salt, a salicylic acid salt, a stearic acid salt, a muconic acid salt, a butyric acid salt, a phenylacetic acid salt, a phenylbutyric acid salt, or a valproic acid salt. In some embodiments, the salt of the compound is a hydrochloric acid salt. In some embodiments, the salt of the compound is formed by reacting the compound with an inorganic acid. In some embodiments, the salt of the compound is formed by reacting the compound with an inorganic acid, wherein the inorganic acid is hydrochloric acid, hydrobromic acid, sulfuric acid, phosphoric acid, or metaphosphoric acid. In some embodiments, the salt of the compound is formed by reacting the compound with an organic acid. In some embodiments, the salt of the compound is formed by reacting the compound with an organic acid, wherein the organic acid is acetic acid, propionic acid, hexanoic acid, cyclopentanepropionic acid, glycolic acid, pyruvic acid, lactic acid, malonic acid, succinic acid, malic acid, L-malic acid, maleic acid, oxalic acid, fumaric acid, trifluoroacetic acid, tartaric acid, L-tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, or valproic acid. In some embodiments, described herein is a hydrochloride salt of a compound that has the structure of Formula (I). In a particular embodiment, the prochlorperazine salt of the invention includes prochlorperazine edisylate, which is a compound comprising prochlorperazine and 1,2-ethanedisulfonate ($^-O_3S(CH_2)_2SO_3^-$).

In another embodiment, the compositions of the invention comprise solvent addition forms of the aforementioned prochlorperazine compounds, e.g., solvates and alcoholates. Solvates contain either stoichiometric or non-stoichiometric amounts of a solvent, and may be formed during the process of crystallization with acceptable solvents such as water, ethanol, and the like. Hydrates are formed when the solvent is water; alcoholates are formed when the solvent is alcohol. Solvates of compounds described herein can be conveniently prepared or formed using routine techniques. In one embodiment, the solvates comprise complexes of the prochlorperazine compound with one or more solvent (e.g., water or alcohol) molecules, or 1 to about 100, or 1 to about 10, or one to about 2, 3 or 4, solvent molecules per molecule of the prochlorperazine compound. In other embodiments, the compounds provided herein can exist in unsolvated as well as solvated forms.

In another embodiment, the compositions of the invention comprise amides or esters of the aforementioned prochlorperazine compounds. The term "amide" refers to a derivative of carboxylic acids in which the hydroxyl group has been replaced by an amine or ammonia. In one embodiment, the amide group is unsubstituted or substituted via the nitrogen atom by alkyl ($C_1$-$C_8$) group, aryl ($C_1$-$C_8$) group, phenyl, carbocyclic ($C_1$-$C_8$) group, heterocyclic ($C_3$-$C_8$) group, acyl, alkyl ($C_1$-$C_8$) halide, or alkenyl ($C_1$-$C_8$) group. The term "ester" refers to a chemical compound derived from an acid (organic or inorganic) in which at least one hydroxyl group is replaced by an alkoxy group. Representative types of "esters" include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl.

In another embodiment, the compositions of the invention comprise isomers of the aforementioned prochlorperazine compounds. The term "isomer" includes compounds with the same formula but a different arrangement of atoms in the molecule. Preferably, the isomers of the prochlorperazine compounds are "tautomers" or "stereoisomers" of the compounds of Formula I. The term "stereoisomer" refers to compounds that differ in the chirality of one or more stereocenters. Stereoisomers include enantiomers and diastereomers. The term "tautomer" refers to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles. Preferably, the tautomers and the stereoisomers of the compounds of Formula I have similar or same biological properties, e.g., with respect to dopamine $D_2$ antagonism, as the parent prochlorperazine compounds.

In some embodiments, the compositions of the invention comprise prodrugs of the aforementioned prochlorperazine compounds. The term "prodrug" refers to any derivative of a compound of the embodiments that is capable of directly or indirectly providing a compound of the embodiments or an active metabolite or residue thereof when administered to a subject. Particularly favored derivatives and prodrugs are those that increase the bioavailability of the compounds of the embodiments when such compounds are administered to a subject (e.g., by allowing a nasally administered compound to be more readily absorbed into the blood) or which enhance delivery of the parent compound to a biological compartment (e.g., the brain) relative to the parent species. Prodrugs include ester forms of the compounds of the invention. Examples of ester prodrugs include formate, acetate, propionate, butyrate, acrylate, and ethylsuccinate derivatives. A general overview of prodrugs is provided in Higuchi et al., Pro drugs as Novel Delivery Systems, Vol. 14 of the American Chemical Society Symposium Series and Edward B. Roche, ed., Bioreversible Carriers in Drug Design, American Pharmaceutical Association and Pergamon Press, 1987, both of which are incorporated herein by reference.

In the aforementioned embodiments, the compositions of the instant invention additionally comprise a nasal carrier. As used herein, the term "nasal carrier" includes solutions, emulsions, suspensions, gels, sols, colloids, and solids, designed for delivery of the aforementioned prochlorperazine compounds to the nasal mucosa. The term "solution" refers to a liquid mixture in which the minor component (e.g., prochlorperazine compound) is uniformly distributed within the major component (e.g., buffer). "Emulsions" refer to a fine dispersion of minute droplets of one liquid in another in which it is not soluble or miscible (e.g., oil and water). "Suspensions" refer to heterogeneous mixtures in which the solute particles do not dissolve but get suspended throughout the bulk of the medium. "Gels" refer to solid jelly-like material that can have properties ranging from soft and weak to hard and tough and are defined as a substantially dilute cross-linked system, which exhibits no flow. "Sols" refer to colloidal suspensions of very small solid particles in a continuous liquid medium. The term "colloid" may be used interchangeably with the terms "gel," "sol," and "suspension" and refers to homogeneous mixtures of ultramicroscopic particles of one substance dispersed through a second substance.

Preferably, the nasal carrier is a liquid. The liquid nasal carrier includes a diluent suitable for application to the nasal mucosa. Suitable diluents include aqueous or non-aqueous diluents or combination thereof. Examples of aqueous diluents include, but are not limited to, saline, water, dextrose or combinations thereof. Non-aqueous diluents include, but are not limited to, alcohols, particularly polyhydroxy alcohols such as propylene glycol, polyethylene glycol, glycerol, and vegetable and mineral oils. These aqueous and/or non-aqueous diluents can be added in various concentrations and combinations to form solutions, suspensions, oil-in-water emulsions or water-in-oil emulsions. In preferred embodiments, the diluent is saline or water.

In one embodiment, the nasal carrier is a saline. The term "saline" refers to substances containing or impregnated with salt, e.g., sodium chloride, potassium chloride, calcium chloride, magnesium chloride, zinc chloride, sodium bicarbonate, calcium bicarbonate, sodium phosphate, calcium phosphate, etc.

In one embodiment, the nasal carrier is a composition comprising citric acid and a chloride salt. Throughout this specification, unless the context requires otherwise, the words "comprise", "comprises" and "comprising" will be understood to imply the inclusion of a stated step or element or group of steps or elements but not the exclusion of any other step or element or group of steps or elements. Thus, wherein the nasal carrier comprises citrate and the chloride salt, the composition may include other elements, e.g., buffers, surfactants, emollients and the like.

As used herein, "citrate" or "citric acid" refers to a citrate anion, in any form, including citric acid (citrate anion complexed with three protons), salts containing citrate anion, and partial esters of citrate anion. Citrate anion is an organic tricarboxylate. Citric acid, which has been assigned Chemical Abstracts Registry No. 77-92-2, has the molecular formula $HOC(CO_2H)(CH_2CO_2H)_2$ and a formula weight of 192.12 g/mol. A citrate salt (i.e., a salt containing citrate anion) is composed of one or more citrate anions in association with one or more physiologically-acceptable cations. Exemplary physiologically-acceptable cations include, but are not limited to, protons, ammonium cations and metal cations. Suitable metal cations include, but are not limited to, sodium, potassium, calcium, and magnesium, where sodium and potassium are preferred, and sodium is more preferred. A composition containing citrate anion may contain a mixture of physiologically-acceptable cations.

In another embodiment, the nasal carrier comprises a partial citrate ester and sodium chloride. A partial ester of a citrate anion will have one or two, but not all three, of the carboxylate (i.e., —$CO_2$—) groups of citrate anion in an ester form (i.e., —COOR, where R is an organic group). In addition to one or two R groups, the partial ester of a citrate anion will include one or two physiologically-acceptable cations (so that the total of the R group(s) and cation(s) equals three). The R group is an organic group, preferably an alkyl (e.g., $C_1$-$C_8$).

The citrate is preferably in association with protons and/or metal cations. Exemplary of such citrate compounds are, without limitation, citric acid, sodium dihydrogen citrate, disodium hydrogen citrate, trisodium citrate, trisodium citrate dihydrate, potassium dihydrogen citrate, dipotassium hydrogen citrate, calcium citrate, and magnesium citrate. In one embodiment, the citrate is present in the base composition in the form of one or more of citric acid, sodium dihydrogen citrate, disodium hydrogen citrate, potassium dihydrogen citrate, or dipotassium hydrogen citrate. In a preferred embodiment, sodium citrate provides the source for the citrate anions. Sodium citrate may be in the form of a dry chemical powder, crystal, pellet or tablet. Any physiologically tolerable form of citric acid or sodium citrate may be used to introduce citrate anions to the composition. For instance, the citric acid or sodium citrate may be in the form of a hydrate, including a monohydrate.

In one embodiment, the amount of citrate in the nasal carrier of the invention is between about 0.001% (by weight or mass) to about 0.50%, particularly between about 0.005% to about 0.1%, especially between about 0.01% to about 0.02%. Thus, in representative embodiments, the amount of citrate in the nasal carrier is about 0.005%, about 0.006%, about 0.007%, about 0.008%, about 0.009%, about 0.01%, about 0.011%, about 0.012%, about 0.013%, about 0.014%, about 0.015%, about 0.016%, about 0.018%, about 0.019%, or a greater percentage by weight of the solvent, e.g., water.

In another embodiment, the invention relates to compositions comprising nasal carriers, wherein the nasal carrier contains a chloride salt. Representative examples of such chloride salts include, e.g., sodium chloride, potassium chloride, calcium chloride, etc. Preferably, the chloride salt is sodium chloride.

In one embodiment, the amount of chloride salt in the nasal carrier of the invention is between about 0.1% (by weight or mass) to about 2.0%, particularly between about 0.5% to about 1.5%, especially between about 0.7% to about 1.2%. Thus, in representative embodiments, the amount of the chloride salt, e.g., sodium chloride in the nasal carrier is about 0.5%, about 0.6%, about 0.7%, about 0.8%, about 0.9%, about 1.0%, about 1.1%, about 1.2%, about 1.3%, about 1.4%, about 1.5%, about 1.6%, about 1.8%, about 1.9%, about 2.0% or a greater percentage by weight of the solvent, e.g., water.

In certain embodiments, the nasal carriers of the invention are acidic. The term "acidic" means that the pH of the composition e.g., aqueous solution, is in the acidic region, below 7.0, particularly below 5.0, especially below 3.0. Thus, in one embodiment, the pH of the solution is between about 2.0 and about 4.0. For example, the pH of the solution may range from about 1.0 to about 6.9 and any values between, including, but not limited to, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9 or more.

In certain embodiments, the nasal carriers of the invention may be buffered. In one embodiment, the buffered nasal carriers of the invention are buffered with acidic buffers, e.g., ethanoates, citrates, lactates, acetates, etc. In another embodiment, the buffered nasal carriers contain zwitterionic buffers, such as, glycine, alanine, valine, leucine, isoleucine and phenylalanine. Buffers designated GRAS (Generally Recognized as Safe) are particularly preferred. Methods of formulating buffered compositions, e.g., via use of a properly calibrated pH probe, are known in the art.

If a buffering agent is employed in the composition, it is chosen in quantities that preferably do not irritate the nasal mucosa. Buffering agents include agents that reduce pH changes. Preferred buffering agents for use in the present invention include, but are not limited to, salts of citrate, acetate, or phosphate. The most preferred buffers include sodium citrate, sodium acetate, sodium phosphate, and/or combinations thereof. Typically, the buffer is added to the compositions of the present invention in quantities of from about 0.01% to about 3% by weight.

In certain embodiments, the nasal carriers of the invention consist essentially of the citrate and the chloride salt. In other embodiments, the nasal carriers of the invention consist of the citrate and the chloride salt. By "consisting of" is meant including, and limited to, whatever follows the phrase "consisting of." Thus, the phrase "consisting of" indicates that the listed elements are required or mandatory. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

These nasal carriers may also contain glucose, sodium bicarbonate, various buffers, and occasionally small amounts of magnesium salts and other salts like acetates, lactates, sulfates and phosphates.

The nasal carrier of the present invention may also contain excipients such as antioxidants, buffering agents, surfactants and/or agents that increase viscosity, provided the excipient is not a chemical preservative. Antioxidants are substances that prevent oxidation of the formulations. Suitable antioxidants for use in the present invention include, but are not limited to, ascorbate, butylated hydroxytoluene, butylated hydroxyanisole, potassium metabisulfite, and the like.

In some embodiments of the present invention, the composition is preservative free. The term "preservative-free" refers to a composition that contains less than 0.5% (as used in typical nasal formulations), particularly less than 0.1%, especially less than 0.01%, including 0.00%, by weight of a preservative selected from benzalkonium chloride, chlorobutanol, methylparaben, ethylparaben, propylparaben, butylparaben, benzyl alcohol, ethylenediaminetetraacetic acid, phenylethyl alcohol, and benzethonium, chlorocresol, chlorhexidine, phenylmercuric nitrate, phenylmercuric borate, phenylmercuric acetate, and thiomersal or combination thereof. Thus, in representative embodiments, the amount of the preservative, e.g., benzalkonium chloride, in the preservative-free nasal carrier is less than about 0.001%, about 0.002%, about 0.005%, about 0.006%, about 0.007%, about 0.008%, about 0.009%, or about 0.01% by weight of the solvent, e.g., water.

The composition may optionally further contain surfactants. Examples of suitable additional surfactants include, for example, anionic surfactants, cationic surfactants, amphoteric surfactants, zwitterionic surfactants, non-ionic surfactants, and combinations thereof. Specific examples of suitable surfactants are known in the art and include those suitable for incorporation into compositions and wipes. The composition may suitably include one or more surfactants in an amount from about 0.01% by weight of the composition to about 2% by weight of the composition. When one or more surfactants is employed, the amount present in the compositions of the invention will vary depending on the particular surfactant chosen, the particular mode of administration (e.g. drop or spray) and the effect desired. In general, however, the amount present will be of the order of from about 0.1 mg/ml to about 10 mg/ml, about 0.5 mg/ml to 5.0 mg/ml, or about 1 mg/ml.

The composition may also further contain additional emulsifiers. For example, natural fatty acids, esters and alcohols and their derivatives, and combinations thereof, may act as emulsifiers in the composition. Other examples of suitable emulsifiers include nonionics such as polysorbate 20, polysorbate 80, anionics such as DEA phosphate, cationics such as behentrimonium methosulfate, and the like. The composition may suitably include one or more emulsifiers in an amount from about 0.01% by weight of the composition to about 2% by weight of the composition.

The pharmaceutical compositions of the present invention may include one or more agents that increase viscosity chosen in quantities that preferably do not irritate the nasal mucosa and increase nasal retention time. Preferred agents that increase viscosity include, but are not limited to, methylcellulose, carboxymethylcellulose sodium, ethylcellulose, carrageenan, carbopol, and/or combinations thereof. The most preferred agents used to increase viscosity and increase nasal retention time is methylcellulose or carbopol. Typically, the agent that increases viscosity is added to the compositions of the present invention in quantities of from about 0.1% to about 10% by weight.

In some embodiments of the present invention, one or more sweetener or flavoring agents are employed. The sweetener or flavoring agent includes any agent that sweetens or provides flavor to the pharmaceutical composition: The sweetener or flavoring agent will mask any bitter or bad taste that may occur if the pharmaceutical composition drips back into the mouth after intranasal administration. By addition of a sweetener or flavoring agent to the intranasal composition, any barrier that a patient may have to taking the intranasal composition because of unpleasant taste is reduced. By adding a sweetener, flavoring agent or masking agent to the intranasal pharmaceutical composition of the present invention, patient compliance is enhanced or improved.

Preferred sweeteners or flavoring agents or masking agents to use in some embodiments of the present invention include, but are not limited to, acacia syrup, anethole, anise oil, aromatic elixir, benzaldehyde, benzaldehyde elixir, cyclodextrins, compound, caraway, caraway oil, cardamom oil, cardamom seed, cardamom spirit, cardamom tincture, cherry juice, cherry syrup, cinnamon, cinnamon oil, cinnamon water, citric acid, citric acid syrup, clove oil, cocoa, cocoa syrup, coriander oil, dextrose, eriodictyon, eriodictyon fluidextract, eriodictyon syrup, aromatic, ethylacetate, ethyl vanillin, fennel oil, ginger, ginger fluidextract, ginger oleoresin, dextrose, glucose, sugar, maltodextrin, glycerin, *glycyrrhiza, glycyrrhiza* elixir, *glycyrrhiza* extract, *glycyrrhiza* extract pure, *glycyrrhiza* fluidextract, *glycyrrhiza* syrup, honey, iso-alcoholic elixir, lavender oil, lemon oil, lemon tincture, mannitol, methyl salicylate, nutmeg oil, orange bitter elixir, orange bitter oilorange flower oil, orange flower water, orange oil, orange peel bitter, orange peel sweet, orange tincture, orange spirit, compound, orange syrup, peppermint, peppermint oil, peppermint spirit, peppermint water, phenylethyl alcohol, raspberry juice, raspberry syrup, rosemary oil, rose oil, rose water, rose water, saccharin, saccharin calcium, saccharin sodium, sarsaparilla syrup, sarsaparilla compound, sorbitol solution, spearmint, spearmint oil, sucrose, sucralose, syrup, thyme oil, tolu balsam, tolu balsam syrup, vanilla, vanilla tincture, vanillin, wild cherry syrup, or combinations thereof.

Most preferred sweeteners to use in some embodiments of the present invention include, but are not limited to, saccharin, sodium saccharin, xylitol, mannitol, sorbitol, sucralose, maltodextrin, sucrose, aspartame, acesulfame potassium, dextrose, glycosides, maltose, sweet orange oil, dextrose, glucose, honey or combinations thereof. Most preferred flavoring agents to use in some embodiments of the present invention include, but are not limited to, glycerin, wintergreen oil, peppermint oil, peppermint water, peppermint spirit, menthol, syrup, or combinations thereof. Most preferred masking agents do not make contact with the taste buds. The preferred masking agent for use in the present invention includes, but is not limited to, cyclodextrins, cyclodextrins emulsions, cyclodextrins particles, cyclodextrins complexes, or combinations thereof.

The compositions of different embodiments of the present invention may of course also include additional ingredients, such as acceptable surfactants, co-solvents, adhesives, agents to adjust the pH and osmolarity.

The composition may additionally include adjunct components conventionally found in pharmaceutical compositions in their art-established fashion and at their art-established levels. For example, the compositions may contain additional compatible pharmaceutically active materials for combination therapy, e.g., one or more additional active agents having a complimentary activity to the activity of prochlorperazine. In one particular embodiment, the invention provides an anti-migraine pharmaceutical composition comprising prochlorperazine and a second agent selected from narcotic analgesics (e.g., oxycodone), nonsteroidal anti-inflammatory drugs (e.g., ibuprofen), barbiturates (e.g., butalbital), ergot derivatives (e.g., dihydroergotamine), selective 5-HT receptor agonists (e.g., sumatriptan). Preferably, the second agent is selected from the group consisting of an anti-emetic (e.g., chlorpromazine or metoclopramide), an ergot (e.g., ergotamine, dihydroergotamine), a triptan (e.g., sumatriptan, rizatriptan, almotriptan, naratriptan, zolmitriptan, frovatriptan, eletriptan) and a pain reliever (e.g., aspirin or acetaminophen).

Pharmaceutical Compositions

In certain embodiments, the compositions of the invention are preservative-free pharmaceutical compositions comprising the prochlorperazine compound with a liquid nasal carrier. The term "pharmaceutical composition" means for the purpose of the present invention any composition which comprises as an active compound, to which is attributed, fully or in part, the therapeutic (e.g., pharmaceutical) effect, at least one of the compounds of the invention or combinations thereof and that may optionally further comprise at least one pharmaceutically acceptable non-active ingredient, as an excipient, carrier or so.

Particularly, the pharmaceutical compositions of the invention are of comparable potency compared to standard formulations or preparations containing prochlorperazine. In one embodiment, the standard formulation is a pharmaceutical composition containing prochlorperazine edisylate (e.g., COMPAZINE). In one embodiment, the pharmaceutical composition has at least 60%, at least 70%, at least 80%, at least 90%, at least 95%, at least 99%, or greater potency compared to a standard formulation. Accordingly, the potency of the pharmaceutical compositions of the invention may be about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.9, or more compared to a pharmaceutical composition containing prochlorperazine edisylate (e.g., COMPAZINE). Methods for determining potency of pharmaceutical preparations containing prochlorperazine, e.g., using in vitro receptor binding assays or in vivo anti-emetic activity assay, are known in the art.

In one embodiment, the pharmaceutical compositions of the invention have a short tailing factor. As is understood in pharmaceutics, "tailing factor" is a measure of peak tailing in a chromatogram. In one embodiment, the tailing factor is defined as the distance from the front slope of the peak to the back slope divided by twice the distance from the center line of the peak to the front slope, with all measurements made at 5% of the maximum peak height.

Thus in one embodiment, the compositions of the invention have a tailing factor of less than 4, particularly less than 3, and especially less than 2. Thus, under this embodiment, the tailing factor of the composition may be about 2, about 1.9, about 1.8, about 1.7, about 1.6, about 1.5, about 1.4, about 1.3, about 1.2, about 1.1, about 1, about 0.9, about 0.8, about 0.7, about 0.6, about 0.5, about 0.3, about 0.2, about 0.1, or less. Compositions of the invention having a tailing factor between about 1.50 to about 1.90, e.g., a tailing factor of about 1.81, about 1.82, about 1.83, about 1.84, about 1.85, about 1.86, about 1.87, about 1.88, about 1.89, about 1.90 are preferred. Methods for determining tailing factors are known in the art. A representative technique using high performance liquid chromatography (HPLC) is described in the Examples section.

In another embodiment, the pharmaceutical compositions of the invention are substantially free of degradation products. The term "degradation product" refers to a compound resulting from a chemical modification of the prochlorperazine compound. The modification, for example, can be the result of a thermally or photochemically induced reaction, including, without limitation, oxidation and hydrolysis. A representative example of a degradation product is prochlorperazine sulfoxide. Methods for determining the degradation products, e.g., using chromatographic separation and analysis, are known in the art.

In one embodiment, the pharmaceutical compositions of the invention comprise less than 10% by weight of the degradation products. Preferably, the pharmaceutical compositions comprise less than 5% by weight of the degradation products. More preferably, the compositions comprise less than 2.5%, less than 1.0%, less than 0.5%, less than 0.1%, less than 0.03%, or even lower % amount by weight of the degradation products.

Embodiments of the invention further relate to stable compositions. In one embodiment, the compositions are stable against oxidation or photodegradation or both oxidation and photodegradation. Under this embodiment, the compositions of the invention are stable for at least 20 days, particularly for at least 30 days, and especially for at least 60 days or more, e.g., at least 120 days. Thus, under one embodiment, the compositions are stable for at least about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 31 days, about 32 days, about 33 days, about 34 days, about 35 days, about 36 days, about 37 days, about 38 days, about 39 days, about 40 days, about 41 days, about 42 days, about 43 days, about 44 days, about 45 days, about 46 days, about 47 days, about 48 days, about 49 days, about 50 days, about 51 days, about 52 days, about 53 days, about 54 days, about 55 days, about 56 days, about 57 days, about 58 days, about 59 days, about 60 days, about 61 days, about 62 days, about 63 days, about 64 days, about 65 days, about 66 days, about 67 days, about 68 days, about 69 days, about 70 days, about 71 days, about 72 days, about 73 days, about 74 days, about 75 days, about 76 days, about 77 days, about 78 days, about 79 days, about 80 days, about 81 days, about 82 days, about 83 days, about 84 days, about 85 days, about 86 days, about 87 days, about 88 days, about 89 days, about 90 days, about 91 days, about 92 days, about 93 days, about 94 days, about 95 days, about 96 days, about 97 days, about 98 days, about 99 days, or more days.

In a related embodiment, the compositions of the invention are chemically stable against oxidation or photo-degradation. Methods for assessing photo-stability and/or oxidative stability of prochlorperazine-containing compositions are known in the art. A representative technique is outlined in the Examples section.

In another related embodiment, the compositions of the invention are microbiologically stable. The term "microbiologically stable" (e.g., spoilage free) means no outgrowth of spoilage bacteria, yeast, fungal and/or mold for at least 30 days, particularly for at least 60 days and especially for at least 90 days before opening. In some embodiments, microbiological stability is further characterized by no appreciable loss of activity, e.g., a loss of activity that is less than 10%, less than 9%, less than 8%, less than 7%, less than 6%, less than 4%, less than 2%, less than 1%, less than 0.9%, less than 0.8%, less than 0.7%, less than 0.6%, less than 0.5%, less than 0.3%, less than 0.2%, less than 0.1%, or less compared to a freshly-prepared composition. In embodiments wherein the compositions are chilled, e.g., at about 4° C., microbiologically stable means no outgrowth of spoilage bacteria, yeast, fungus or mold and no appreciable loss of activity for a period up to 2 months, 3 months, 4 months, 5 months, 6 months, or more.

Methods for Making the Pharmaceutical Compositions and/or Formulations

The composition in some embodiments of the present invention can be made, for example, e.g., by mixing the prochlorperazine compound with a carrier. Wherein the composition is a liquid composition, the active ingredient containing the prochlorperazine compound may be dissolved in an aqueous vehicle, e.g., saline solution. Preferably, the vehicle is a nasal carrier containing the chloride salt and the citrate, the respective amounts of the components being described previously. The active ingredient may be dissolved in the carrier optionally together with a sweetener, flavoring agent, or masking agent or combinations thereof at room temperature under aseptic conditions to form a mixture. It will be understood by those of ordinary skill in the art that the order of mixing is not critical, and the present invention includes without limitation mixing of the formulation in any order. Additionally, the mixture may be filtered, e.g., sterile filtered using 0.22 μm gauze and stored in the devices or articles of the invention.

In one embodiment, the liquid compositions are buffered using one or more strategies described previously. Preferably, the liquid compositions are buffered at an acidic pH, for example, using an acid such as hydrochloric acid (HCl). In these embodiments, the final pH of the aqueous composition may be maintained between about 2.0 and about 4.0, particularly between about 2.5 and about 3.0, e.g., a pH of about 2.2, about 2.3, about 2.4, about 2.5, about 2.6, about 2.7, about 2.8.

In the aforementioned embodiments, the compositions and formulations will preferably contain an effective amount of the prochlorperazine compound. The amount of prochlorperazine compound (e.g., effective dose) will depend on the particular compound and the carrier that are selected, the subject to be treated, the desired frequency of administration, and the effect desired. As used herein, an effective amount of the composition includes that amount effective to achieve the relief or palliation of symptoms, condition and/or disability associated with a disease. In some embodiments, the effective amount of the prochlorperazine compound in the composition may range from about 10 ng to about 20 mg, particularly between about 100 ng to about 5 mg, and especially between about 0.5 mg to about 2.0 mg, including any values between, for example, 10 μg, 20 μg, 30 μg, 40 μg, 50 μg, 60 μg, 70 μg, 80 μg, 90 μg, 100 μg, 200 μg, 300 μg, 400 μg, 500 μg, 600 μg, 700 μg, 800 μg, 900 μg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 10.5 mg, 11 mg, 11.5 mg, 12 mg, 12.5 mg, 13 mg, 13.5 mg, 14 mg, 14.5 mg, 15 mg, 15.5 mg, 16 mg, 16.5 mg, 17 mg, 17.5 mg, 18 mg, 18.5 mg, 19 mg, 19.5 mg, 20 mg or more.

Wherein the composition of the invention is a liquid composition, e.g., a solution of prochlorperazine in buffered saline, the concentration of the prochlorperazine compound may range from about 0.1 mg/ml to about 20 mg/ml, particularly between about 500 μg/ml to about 10 mg/ml, and especially between about 2 mg/ml to about 10 mg/ml including any values between, for example, 100 μg/ml, 200 μg/ml, 300 μg/ml, 400 μg/ml, 500 μg/ml, 600 μg/ml, 700 μg/ml, 800 μg/ml, 900 μg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 10.5 mg/ml, 11 mg/ml, 11.5 mg/ml, 12 mg/ml, 12.5 mg/ml, 13 mg/ml, 13.5 mg/ml, 14 mg/ml, 14.5 mg/ml, 15 mg/ml, 15.5 mg/ml, 16 mg/ml, 16.5 mg/ml, 17 mg/ml, 17.5 mg/ml, 18 mg/ml, 18.5 mg/ml, 19 mg/ml, 19.5 mg/ml, 20 mg/ml or more.

In one embodiment, the compositions and formulations of the invention are prepared extemporaneously. For example, first a 1.0 L preservative-free vehicle is prepared by adding 0.1 grams of citric acid and 9 grams of sodium chloride in deionized water. The solution is then transferred to a container and the pH is adjusted to 2.5 with hydrochloric acid (0.1 N). Pharmaceutical grade prochlorperazine edisylate powder (250 mg) is then added to 50 mL of the vehicle until the drug is dissolved and a clear solution is formed. The resulting solution is filtered using 0.22 μm nylon syringe filters in a laminar flow hood and transferred into an opaque white previously-sterilized nasal spray bottles. The bottles can be sterilized under ultraviolet light for 1 hour and rinsed with the sterile preservative free vehicle.

Kits/Articles Containing the Compositions

In certain embodiments, the instant invention provides for kits comprising the compositions of the invention comprising the prochlorperazine compound with a liquid nasal carrier, optionally together with instructions for formulating a nasal spray or the nasal drop comprising the prochlorperazine compound. The components of the kit, e.g., the prochlorperazine compound and the liquid nasal carrier may be provided in one or separate compartments, optionally together with other ingredients, e.g., gelling agents, emollients, surfactants, humectants, viscosity enhancers, emulsifiers, etc., in one or more compartments. The kits may optionally comprise instructions for formulating the compositions and/or using the components, either individually or together, in the treatment of migraines.

In a related embodiment, the present invention provides kits comprising an article (e.g., devices for nasal spraying or nasal dropping) comprising the aforementioned compositions. Alternately, the kits may include the individual components, e.g., the compositions and the articles for administration of the compositions, separately, optionally together with secondary information for using the components.

In some embodiments, the instant invention provides for articles and devices that are filled with single or multidose amounts of the compositions of the invention. Preferably, the device is filled with one single dose of the compositions. In a preferred embodiment, the container holding the pharmaceutical composition and its sealing means are sterilizable, most preferably, at least parts of the device that are in contact with the composition is constructed and assembled in a configuration that can be sterilized. Devices with one or more unit-dose(s) can be sterilized either before or after packaging, employing methods and technology that are well known in the art. Individual devices can be packaged, sterilized and shipped; alternatively, entire shipping and storage packages can be sterilized at once, and the devices removed individually for dispensing, without affecting the sterility of the remaining units.

Methods for Administering the Compositions

Pharmaceutical compositions of the present invention can be administered intranasally by nasal spray, drop, solution, suspension, gel, and the like. In one embodiment, the pharmaceutical composition of the present invention is a sterile solution or suspension, which is administered as a nasal spray or as nasal drops, using devices known in the art. Representative examples include, e.g., nebulizers that are capable of delivering selected volumes of formulations as liquid-droplet aerosols. For example, a commercially available spray pump with a delivery volume between about 10 μl and about 200 μl, particularly between about 50 μl and about 100 μl, is available from Aptar Pharma, Inc. (Congers, N.Y.). The spray tips are adjustable for adult size and pediatric size. In one embodiment, the composition comprising the prochlorperazine compound and the nasal carrier is co-administered intranasally via an aerosol spray in a daily volume of between 30 μl to 500 μl.

Similarly, wherein the formulation is adapted as a nasal drop, a variety of devices may be employed in the administration of the compositions of the invention, including, e.g., pipettes, rhinyle catheter and squirt tubes, squeeze bottles, metered-dose spray pumps, spray devices, nasal pressurized metered-dose inhalers (pMDIs). See, the review article by Djupesland et al. entitled "Nasal drug delivery devices: characteristics and performance in a clinical perspective" (*Drug Deliv Transl Res.*, 3(1): 42-62, 2013).

When the pharmaceutical composition is a liquid, preferred volumes of the liquid are absorbed through the nasal mucosa. The volume of the liquid includes volumes of from about 0.025 ml to about 2 ml, particularly from about 0.25 ml to 1 ml, and especially from about 0.3 ml to about 0.5 ml for adults. For small children, the volume of the liquid includes 0.05 ml to about 1 ml or less. However, the pharmaceutical compositions of the present invention are not limited to one particular volume.

Applications of the Compositions

In one embodiment, the compositions and formulations of the invention are useful in the treatment of a disease. As used herein, the term "treat" or "therapy" refers to administering a regimen to the subject, e.g., the administration of the pharmaceutical composition of the instant invention, such that at least one symptom of the disorder is healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder.

The term "disease" or "disorder" as used herein includes any central nervous system disorder characterized by headaches. Particularly, the "disease" of the invention includes migraine. Migraine includes the common or classical type as well as migraine variants which would be familiar to one skilled in the art. According to the current International Headache Society's classification system, there are seven types of migraine, including migraine with aura, migraine without aura, migraine without headache, familial hemiplegic migraine, migraine with brainstem aura, retinal migraine, and chronic migraine.

In certain embodiments, subjects are treated until a therapeutic endpoint is achieved. Methods for determining endpoints in therapy of migraine are known in the art. In one embodiment, the endpoint comprises a reduction of at least about 40%, about 50%, about 60%, about 70%, about 80%, about 90%, about 95%, about 99%, or more in the pain score. In another embodiment, the effectiveness of the treatment is assessed with a migraine disability assessment score (MIDAS). Still in other embodiments, the subjects are administered a dose of the pharmaceutical composition of the present invention that effectively elicits analgesia or anesthesia. Preferably, the dose does not cause undesirable or intolerable side effects such as respiratory depression.

In one embodiment, "treatment" or "therapy" of the migraine disease comprises reducing the incidence, frequency, duration or grade of a symptom associated with migraine. In such embodiments, the symptom is preferably selected from the group consisting of headaches, nausea, vomiting, and sensitivity to light or a combination thereof.

In one embodiment, the compositions of the invention are useful for the therapy of migraine without aura (formerly called common migraine). This variant is characterized by moderate to severe pulsating headache pain that occurs without warning and is usually felt on one side of the head, along with nausea, confusion, blurred vision, mood changes, fatigue, and increased sensitivity to light, sound, or smells. Attacks typically last 4-72 hours, and repeat a few times a year to a few times a week. Movement generally makes the attack worse.

In another embodiment, the compositions of the invention are useful for the therapy of migraine with aura (formerly called classic or complicated migraine). This variant is characterized by visual disturbances and other neurological symptoms that appear about 10 to 60 minutes before the actual headache and usually last no more than an hour. Partial, temporary vision loss may be observed in some subjects. The aura may occur without headache pain, which can strike at any time. Less frequent aura symptoms include an abnormal sensation, numbness, or muscle weakness on one side of the body; a tingling sensation in the hands or face; trouble speaking; and confusion. Nausea, loss of appetite, and increased sensitivity to light, sound, or noise may precede the headache. Migraine aura can also occur without a headache.

In another embodiment, the compositions of the invention are useful for the therapy of migraine with brainstem aura, (formerly called Basilar-type migraine). This variant mainly affects children and adolescents and is characterized by aura symptoms that originate from the brainstem. Symptoms include partial or total loss of vision or diplopia, dizziness and vertigo, poor muscle coordination, slurred speech, tinnitus, and syncope. Many factors can trigger migraine headache attacks, including alteration of sleep-wake cycle; missing or delaying a meal; medications that cause a swelling of the blood vessels; daily or near daily use of medications designed for relieving headache attacks; bright lights, excessive exposure to sunlight, video games, TV and movie viewing; certain foods; and excessive noise. Stress and or underlying depression are also known trigger factors of migraine.

In carrying out the use embodiments of the invention, the compositions are designed for nasal or nasolacrimal administration. Alternatively, the compositions may be administered to a subject using other delivery routes, e.g., oral, ocular, inhalation or pulmonary, oral cavity (sublingual or Buccal cell) or cerebral spinal fluid (CSF), etc. Preferably, the route of administration is nasal or nasolacrimal.

The compositions and formulations of the invention may be administered to a variety of subjects or patients. As used herein, the term "subject" or "patient" includes any member of the subphylum chordata, including, without limitation, humans and other primates, including non-human primates, e.g., chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

The following examples are provided to further illustrate the embodiments of the present invention, but are not intended to limit the scope of the invention. While they are typical of those that might be used, other procedures, methodologies, or techniques known to those skilled in the art may alternatively be used.

EXAMPLES

Example 1

Formulation of Prochlorperazine Nasal Spray

PFP nasal spray was formulated by dissolving 250 mg of prochlorperazine edisylate in 50 mL of the preservative-free vehicle (0.5% w/v). The preservative free vehicle consists of 0.01% citric acid in 0.9% sodium chloride solution in deionized water; the final pH of the buffer is adjusted to 2.5 with dilute hydrochloric acid (0.1 N). The formulation was sterile filtered using 0.22 µm nylon syringe filters and filled in 60 mL capacity natural low-density polyethylene nasal spray bottles laminar airflow workbench (Labconco, Kansas City, Mo., USA).

Example 2

Stability Studies Using High Performance Liquid Chromatography (HPLC)

The mobile phase consisted of the ion-pairing solution, acetonitrile, and methanol (50:40:10). The ion pairing solution was previously prepared by dissolving 4.33 g of sodium-1-octanesulfonic acid and 4.0 mL glacial acetic acid in 1000 mL of water. The chromatographic separation was achieved using a 3.9 mm×15 cm L1 (C18) column with 5 µm particle size. The flow-rate was 1.5 mL per minute and detection wavelength was 254 nm. The HPLC analysis was carried out by injecting 20 µL of sample into the Waters Alliance HPLC with Waters photodiode array (PDA) detector. Data acquisition and analysis was performed using WATERS® EMPOWER 3 software. The HPLC method was validated according to International Council on Harmonization (ICH) guidelines for various parameters including: linearity, accuracy and precision, robustness, and ruggedness. A standard 5-point calibration curve was constructed by linear regression of the ratios of the peak areas of the prochlorperazine maleate peak to the internal standard peak (trifluoperazine hydrochloride) obtained from standard solutions at concentrations of 0.01, 0.05, 0.1, 0.2, and 0.25 mg/mL ($R^2$=0.9989). For all chromatograms, USP system suitability parameters such as USP tailing factor, USP resolution (R) between prochlorperazine and the internal standard, and USP plate count were calculated using Empower 3 (WATERS®, Milford, Mass.) software.

The stability indicating assay for PFP nasal spray was developed using prochlorperazine sulfoxide, a major degradation product of prochlorperazine, to indicate and identify degradation in samples of prochlorperazine. To obtain a baseline for the measurement of this major degradation product, prochlorperazine sulfoxide was added at a concentration of 0.1 mg/mL to a standard solution of prochlorperazine edisylate (0.1 mg/mL) and trifluoperazine (0.09 mg/mL) and injected into the HPLC. The specificity of the HPLC method to degradation products was also assessed by subjecting prochlorperazine to various forced degradation conditions such as hydrolysis, oxidation, photodegradation, thermal degradation and UV irradiation. Forced degradation studies involved treatment of 0.1 mg/mL prochlorperazine edisylate with 0.1 M hydrochloric acid for 1 hour to assess for acid hydrolysis, 0.1 M sodium hydroxide for 1 hour to assess for alkaline hydrolysis, 0.1 M hydrogen peroxide overnight to assess for oxidation, ultraviolet radiation (UV light of Labconco biological safety cabinet) overnight to assess for UV irradiation, laboratory light overnight to assess for photostability and 60° C. temperature (using a laboratory hot plate) overnight to assess for thermal stability.

The HPLC method showed that the relative retention times for USP standard prochlorperazine maleate and USP internal standard trifluoperazine are 1.0 and 1.2 respectively. A freshly prepared solution of Prochlorperazine edisylate was also analyzed using the HPLC method and was compared with USP standard prochlorperazine maleate. Prochlorperazine edisylate peaks eluted at the same time as that of USP standard prochlorperazine maleate and the potency of prochlorperazine edisylate was 99.7±2.3%. The chromatograms showed sharp and distinct peaks for each analyte without interference from other substances such as solvents etc.

The USP suitability parameters were evaluated and the results showed that the tailing factor was 1.87 (USP specification—the tailing factor is not more than 227), the resolution between prochlorperazine and trifluoperazine was 5.38 (USP specification—the resolution between prochlorperazine and internal standard is not less than 227) and the relative standard deviation for replicate injections was 0.21% (USP specification—the relative standard deviation for replicate injections is not more than 2%27). These results indicate the positive suitability of the HPLC method for the assay of prochlorperazine in PFP nasal spray. The standard curve of prochlorperazine edisylate was linear over the range of concentrations ($R^2$=0.999). Results from the validation studies showed that the parameters of accuracy, precision, robustness and ruggedness were within the specified limits outlined in the validation of analytical procedures, International Conference of Harmonisation (ICH) guidelines.

Oxidation and photodegradation are major degradation pathways of prochlorperazine and usually result in the formation of prochlorperazine sulfoxide as major degradant.10 Therefore, it is desired that the HPLC method utilized for evaluating the stability of prochlorperazine be able to identify prochlorperazine sulfoxide clearly. The HPLC method used in this study was able to resolve prochlorperazine sulfoxide distinctly from prochlorperazine edisylate and trifluoperazine. The relative retention times of prochlorperazine sulfoxide, prochloperazine edisylate, and internal standard were 1.0, 3.5, and 4.5 respectively (FIG. 1). Furthermore, forced degradation studies were also performed to assess any other degradation pathways that may interfere with prochlorperazine assay. Oxidation and UV irradiation were the only pathways that showed degradation of prochlorperazine. The additional peaks associated with degradation products did not co-elute with the prochlorperazine peak. The other degradation conditions including: acid hydrolysis, base hydrolysis, photodegradation, and thermal degradation did not show prochlorperazine degradation and resulted in intact peaks. These results indicated that the HPLC method developed has the potential to identify major degradants of prochlorperazine and can be successfully utilized for stability studies of PFP nasal spray.

Example 3

Analysis of Chemical Stability

For chemical stability sample analysis, five bottles of 0.5% w/v (5 mg/mL) prochlorperazine nasal spray which were prepared as described above were placed on a dry ventilated surface of the lab at room temperature (22.7±0.8° C., relative humidity (RH)–32.5±5%). At time intervals, 0, 20, 30, 45, and 60, and 120 days, a 100 µL aliquot of nasal spray was pipetted into a 15 mL centrifuge tube. This solution was spiked with 20 µL of 22.5 mg/mL internal standard (trifluoperazine) solution and the mixture was diluted with preservative-free vehicle to obtain a final concentration of 0.1 mg/mL of prochlorperazine and 0.09 mg/mL internal standard. The final solution was then injected in HPLC for analysis. The percentage assay values for stability samples were calculated using calibration curve described above using ratios of the peak areas of prochlorperazine and trifluoperazine obtained after integrating peaks from chromatograms of stability samples. The percentage assay of prochlorperazine nasal spray at 120 days was >90% indicating the satisfactory chemical stability of prochlorperazine nasal spray. However, the chromatogram revealed the presence of degradant prochlorperazine sulfoxide at low concentrations (<4%) indicating degradation of prochlorperazine (FIG. 2). In addition, some unknown peaks were also present in chromatograms of 60-day sample indicating the presence of other degradation products (FIG. 3).

Example 4

Test for Physical Stability

Drug product tests such as color and clarity, pH, and viscosity were also performed at all time points studied under chemical stability tests. The samples were visually inspected against black and white backgrounds using a high-intensity lamp at each time point to evaluate the characteristics of color and clarity. The pH meter, calibrated with standard buffer solutions of pH 4, 7, and 10 was used for pH analysis. The viscosity measurements were performed using a Brookfield Dial Viscometer, at the Department of Pharmaceutics and Pharmaceutical Chemistry, University of Utah, Salt Lake City, Utah. The 5 mg/mL PFP nasal spray stored in low-density polyethylene bottles at room temperature demonstrated good physical and chemical stability for up to 120 days.

Example 5

Analysis of Microbiological Stability

For microbiological stability analysis, five bottles of prochlorperazine nasal spray which were prepared as described above were placed on a ventilated surface of the lab at room temperature (22.7±0.8° C., RH–32.5±5%). The microbiological stability was performed at 0, 30, and 60 days after storage. To ascertain microbiological stability samples were subjected to tests described under USP <51>29 and USP <61>30.

USP <51> illustrates the antimicrobial effectiveness testing of aqueous-based, topical, oral, ophthalmic, otic, nasal, irrigation, and dialysis fluids.29 The testing procedure and criteria for effectiveness for prochlorperazine nasal spray was based on tests and limits specified under category 1 (injections, sterile nasal products, ophthalmic products, etc.) outlined in USP <51>.29 The following microorganisms were used in the test; bacteria: *Staphylococcus aureus* (ATCC No. 6538), *Pseudomonas aeruginosa* (ATCC No. 9027), *Escherichia coli* (ATCC No. 8739), yeast: *Candida albicans* (ATCC No. 10231) and fungi: *Aspergillus brasiliensis* (ATCC No. 16404). The test strains of microorganisms were harvested and cultured using growth medium and procedures outlined under preparation of test strains in USP <51>.29 Tryptic soy broth was used to grow bacteria and potato dextrose agar was used to grow yeast and fungi. For antimicrobial effectiveness testing, 1 mL of the prochlorperazine nasal spray was added to 9 mL of phosphate buffered saline (pH—7.4) in a sterile tube. These tubes were inoculated with test microorganisms to obtain a final concentration of $1 \times 10^5$ colony-forming unit (CFU)/mL. The samples were then incubated at temperatures 36±1° C. for bacteria and 30±2° C. for yeast and fungi. At days 0, 14, and 28, samples were collected, and the number of CFU present in each test and control were determined by the plate-count procedure. Using the calculated concentrations of CFU/mL present at the start of the test, change in log 10 values of the concentration of CFU/mL for each microorganism at 14, and 28 days were calculated, and the change in concentration was expressed in terms of log reduction. A neutralization validation study was performed before the test to rule out any possible antimicrobial properties of the drug prochlorperazine present in the nasal spray.

The test described in USP <61> allows quantitative enumeration of mesophilic bacteria and fungi that may grow under aerobic conditions in nonsterile products.30 All test organisms for USP <61> were harvested and cultured as described above under USP <51>. USP <61> tests included *Bacillus subtilis* (ATCC No. 6633) and excluded *Escherichia coli* (ATCC No. 8739). The nasal spray bottles used in USP <51> were also used for USP <61> and the sampling procedure was the same as described under USP <51>. For actual testing, a 1:10 ratio of the prochlorperazine nasal spray in Dey/Engley (D/E) broth was prepared and the dilutions were plated to determine resulting total aerobic mold and bacterial concentrations using plate-count method. Additionally, a neutralization validation assay was performed to determine if D/E broth is a sufficient neutralization broth, and did not affect the viability of any microorganisms used in the current study. To verify testing conditions, the preservative-free vehicle was added to D/E broth as a negative control. All microbiological analyses were performed at Antimicrobial Test Laboratories (now Microchem Laboratory), a Good Laboratory Practice (GLP) certified lab for microbiological analysis, Round Rock, Tex., USA.

Due to their direct interaction with mucosal surfaces, it is required that nasal spray formulations are devoid of any microbial contamination. Therefore, it is important to demonstrate through appropriate testing that the nasal spray does not support the growth of microorganisms (bacteria, yeast, and mold) and microbiological quality is maintained throughout the expiration dating period. Because our formulation does not contain any preservatives, demonstration of microbiological effectiveness is crucial by performing a microbial challenge assay specified in USP <51>. The results from USP <51> showed that both 30-day and 60-day sample passed the antimicrobial effectiveness testing based on the criteria for nasal spray (category 1) provided in USP <51>. According to the USP limits, there must be not less than (NLT) 3 log reduction from the initial calculated count at 14 days, and there must be no increase from 14 days' count at 28 days for bacteria and there must not be any increase from the initial calculated count at 14, and 28 days for yeast and molds. Our results indicated that, for both 30-day and 60-day samples the log reduction from the initial calculated count at 14 days greater than 3 and no increase from 14 days count at 28 days was observed for bacteria. In addition, no significant increase in yeast and mold count from initial count was observed for both samples.

In addition to antimicrobial effectiveness tests, quantitative microbiological enumeration tests involving mesophilic aerobic bacteria and fungi were performed on 30-day and 60-day samples of PFP nasal spray. The tests were described under USP <61> and the limits for nasal spray specify that the total aerobic microbial count (TAMC) does not exceed 25 CFU/mL and the total combined yeasts and mold count (TYMC) does not exceed 25 CFU/mL. Our USP<61> testing results showed that for 30-day samples the TAMC and TYMC were <10 CFU/mL. For 60-day samples, the TAMC and TYMC were <5 CFU/mL. The results from both USP<51> and USP <61> indicate that the PFP nasal spray was microbiologically stable for up to a 60-day period with no signs of microbial growth or contamination. Similar to chemical stability data, microbiological stability data can be utilized to assign beyond-use dates if PFP nasal spray is compounded extemporaneously.

Example 6

In Vivo Efficacy of PFP Nasal Spray in Migraine Animal Model

The in vivo antimigraine efficacy of the PFP nasal spray after intranasal administration will be evaluated in potassium chloride (KCl) induced cortical spreading depression (CSD) model in C57Bl/6 mice. The efficacy of PFP nasal spray will also be compared with the efficacy of currently used IMITREX® (Sumatriptan) nasal spray. Briefly, animals will be randomly divided into control (n=5), PFP nasal spray (5 mg/mL), and IMITREX® (5 mg/mL) groups. Each animal will then be anesthetized with isoflurane (5% induction, 1.4%-1.7% maintenance) and will be mounted on a stereotaxic frame. The parietal skull will be exposed between bregma and lambda, and the region 1 mm postrerolateral to bregma, anterolateral to lambda, and medial to the temporal ridge will be thinned to transparency. A burr hole will be created 0.5 mm from the temporal ridge, midway between bregma and lambda for KCl solution application. The cortex will be illuminated by a white light-emitting diode (LED) and reflected light (optical intrinsic signal, OIS) will be collected with a lens system. CSDs will then be induced by continuous perfusion of 1 M KCl using a syringe pump (1 ml/h) delivered for 15 minutes before drug treatment as an internal control. After CSDs were established, control, PFP nasal spray, and IMITREX® will be administered intranasally using a micropipette in a blinded manner and CSDs will be further induced and recorded for an additional 60 min via continuous perfusion of 1M KCl. CSDs will be identified by multiphasic concentric changes in OIS. The efficacy of PFP nasal spray will then be evaluated by comparing the reduction in CSD number in groups treated with control and IMITREX®.

Example 7

Pharmacokinetics and Bio-Distribution of PFP Nasal Spray in Animals

The plasma pharmacokinetics and tissue biodistribution of prochlorperazine after intranasal administration and oral administration will be evaluated in mice using liquid chromatography-mass spectroscopy (LC/MS). Briefly, mice will be fasted overnight, and PFP nasal spray will be administered intranasally using a micropipette or orally using an oral gavage needle. At time points 0, 0.5, 1, 2, 4, 6, 8, 12, and 24 hrs. animals will be euthanized, and blood, brain, liver, spleen, lungs, kidneys, heart will be collected. The plasma from the blood will be isolated by centrifugation, and the tissues will be homogenized using a tissue homogenizer. Prochloperazine from plasma and tissue homogenate will then be extracted using solid-phase extraction and then injected into LC/MS for quantification of prochlorperazine. It is expected that the concentrations of prochloperazine in brains of mice after intranasal administration will be higher when compared to the brains of mice where prochlorperazine is administered orally. Furthermore, other pharmacokinetic parameters such as maximum plasma concentration (Cmax), peak concentration time (Tmax), plasma half-life (T½), and Area Under the Curve (AUC) will be compared between the intranasal administration and oral administration of prochloperazine using PHOENIX® WINNONLIN® pharmacokinetic software.

Other Embodiments

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described in the foregoing paragraphs. In addition, the materials, methods, and examples are illustrative only and not intended to be limiting. In case of conflict, the present specification, including definitions, will control.

All United States patents and published or unpublished United States patent applications cited herein are incorporated by reference. All published foreign patents and patent applications cited herein are hereby incorporated by reference. All published references, documents, manuscripts, scientific literature cited herein are hereby incorporated by reference. All identifier and accession numbers pertaining to Chemical Abstracts Registry databases that are cited herein are hereby incorporated by reference.

I claim:

1. A preservative-free pharmaceutical composition comprising, as an active ingredient, prochlorperazine or a derivative thereof or a salt thereof, or a hydrate thereof, or an alcoholate thereof, or a tautomer thereof, or a stereoisomer thereof, and a nasal carrier,
    wherein the nasal carrier comprises an aqueous solution containing 0.005% to 0.5% by weight citric acid and 0.5% to 2.0% by weight sodium chloride, and the aqueous solution has a pH value of 2.0 to 4.0.

2. The pharmaceutical composition of claim 1, wherein the salt of prochlorperazine comprises prochlorperazine edisylate.

3. The pharmaceutical composition of claim 1, which consists of prochlorperazine or a derivative thereof or a salt thereof, or a hydrate thereof or an alcoholate thereof, or tautomer thereof, or a stereoisomer thereof and a nasal carrier.

4. The pharmaceutical composition of claim 1, wherein the composition is free of preservatives selected from the group consisting of benzyl alcohol, benzalkonium chloride, benzethonium chloride, chlorobutanol, methylparaben, propyl paraben, ethylenediaminetetraacetic acid, chlorocresol, chlorhexidine, phenylmercuric nitrate, phenylmercuric borate, phenylmercuric acetate, and thiomersal, or a combination thereof.

5. The pharmaceutical composition of claim 1, which has a potency greater than about 99% compared to a standard composition comprising prochlorperazine maleate.

6. The pharmaceutical composition of claim 1, which is free of degradation products.

7. The pharmaceutical composition of claim 6, wherein the degradation product is prochlorperazine sulfoxide.

8. The pharmaceutical composition of claim 1, which is stable for up to 20 days.

9. The pharmaceutical composition of claim 8, which is stable against oxidation and photodegradation.

10. The pharmaceutical composition of claim 1, which is microbiologically stable.

11. The pharmaceutical composition of claim 10, which is microbiologically stable for up to 30 days.

12. The pharmaceutical composition of claim 1, wherein the dose of the active ingredient is between about 1 mg to about 10 mg.

13. The pharmaceutical composition of claim 1, wherein the dose of the active ingredient is between about 2 mg/ml to about 8 mg/ml.

14. A method for the preparation of a pharmaceutical composition of claim 1, comprising mixing prochlorperazine or a derivative thereof or a salt thereof, or a hydrate thereof or an alcoholate thereof, or tautomer thereof, or a stereoisomer thereof with at least one nasal carrier,
    wherein the nasal carrier comprises an aqueous solution containing 0.005% to 0.5% by weight citric acid and 0.5% to 2.0% by weight sodium chloride, and the aqueous solution has a pH value of 2.0 to 4.0.

15. The method of claim 14, wherein the salt of prochlorperazine comprises prochlorperazine edisylate.

16. A method for treating, ameliorating, or reducing the frequency, incidence or symptoms of migraine comprising administering to a subject in need thereof, an effective amount of the pharmaceutical composition of claim 1.

17. The method of claim 16, wherein the method comprises administering the aqueous composition intranasally.

\* \* \* \* \*